United States Patent
Lee et al.

(10) Patent No.: US 12,227,513 B2
(45) Date of Patent: Feb. 18, 2025

(54) SALT AND CRYSTALLINE FORM OF FUROPYRIMIDINE COMPOUND AND PHARMACEUTICAL USE THEREOF

(71) Applicant: TIUMBIO CO., LTD., Seongnam-si (KR)

(72) Inventors: Minhee Lee, Seongnam-si (KR); Seon-Mi Kim, Seongnam-si (KR); Hun-Taek Kim, Seongnam-si (KR)

(73) Assignee: TIUMBIO CO., LTD., Seongnam-si (KR)

( * ) Notice: Subject to any disclaimer, the term of this patent is extended or adjusted under 35 U.S.C. 154(b) by 881 days.

(21) Appl. No.: 17/296,836

(22) PCT Filed: Oct. 25, 2019

(86) PCT No.: PCT/KR2019/014164
§ 371 (c)(1),
(2) Date: May 25, 2021

(87) PCT Pub. No.: WO2020/111524
PCT Pub. Date: Jun. 4, 2020

(65) Prior Publication Data
US 2022/0002312 A1 Jan. 6, 2022

(30) Foreign Application Priority Data
Nov. 30, 2018 (KR) .......... 10-2018-0151990

(51) Int. Cl.
*C07D 491/20* (2006.01)
(52) U.S. Cl.
CPC ........ *C07D 491/20* (2013.01); *C07B 2200/13* (2013.01)
(58) Field of Classification Search
CPC ................................................. C07D 491/20
See application file for complete search history.

(56) References Cited

U.S. PATENT DOCUMENTS 9,481,684 B2 * 11/2016 Kim .................. A61P 17/14

FOREIGN PATENT DOCUMENTS

| | | | |
|---|---|---|---|
| JP | 2016-518443 A | 6/2016 | |
| JP | 2016-527238 A | 9/2016 | |
| JP | 2017-520565 A | 7/2017 | |
| KR | 10-2001-0090430 A | 10/2001 | |
| KR | 10-2002-0045609 A | 6/2002 | |
| KR | 10-2011-0056242 A | 5/2011 | |
| KR | 10-2013-0102002 A | 9/2013 | |
| KR | 10-2018-0015264 A | 2/2018 | |
| WO | 2014/184778 A1 | 11/2014 | |
| WO | 2015/010641 A1 | 1/2015 | |
| WO | 2016/010809 A1 | 1/2016 | |

OTHER PUBLICATIONS

Gupta, Review: Salts of Therapeutic Agents: Chemical, Physicochemical, and Biological Considerations, 2018, Molecules, vol. 23, p. 1-15 (Year: 2018).*
Berge, Review Article: Pharmaceutical Salts, 1977, Journal of Pharmaceutical Sciences, vol. 66, No. 1, p. 1-19 (Year: 1977).*
International Searching Authority, International Search Report of PCT/KR2019/014164 dated Jan. 29, 2020 [PCT/ISA/210].

* cited by examiner

*Primary Examiner* — Kamal A Saeed
*Assistant Examiner* — Karen Cheng
(74) *Attorney, Agent, or Firm* — Sughrue Mion, PLLC (57) ABSTRACT

Salts and crystalline forms of (R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidine]-3(2H,4H,7H)-yl)-1-phenylethyl)amino)butanoic acid (formula (1)) show excellent physicochemical properties including, for example, hygroscopicity, related substances, chemical stability. The salts and crystalline forms are useful and suitable for pharmaceutical uses such as the preparation of a pharmaceutical composition containing the same as an active ingredient.

15 Claims, 4 Drawing Sheets

SALT AND CRYSTALLINE FORM OF FUROPYRIMIDINE COMPOUND AND PHARMACEUTICAL USE THEREOF

CROSS REFERENCE TO RELATED APPLICATIONS

This application is a National Stage of International Application No. PCT/KR2019/014164 filed on Oct. 25, 2019, claiming priority based on Korean Patent Application No. 10-2018-0151990 filed on Nov. 30, 2018.

TECHNICAL FIELD

The present invention relates to salts and crystalline forms of a furopyrimidine compound, and pharmaceutical uses thereof. More specifically, the present invention relates to salts and crystalline forms of (R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidin]-3 (2H,4H,7H)-yl)-1-phenylethyl)amino)butanoic acid, and pharmaceutical uses thereof.

BACKGROUND ART

The compound of Formula 1, whose name is (R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidine]-3 (2H,4H,7H)-yl)-1-phenylethyl)amino)butanoic acid, is disclosed in Korean Patent No. 1495260 and U.S. Pat. No. 9,481,684. It is known that this compound acts as a gonadotropin-releasing hormone (GnRH) receptor antagonist and thus are useful in preventing or treating various sex hormone-related symptoms.

[Formula 1]

DISCLOSURE OF INVENTION

Technical Problem

The compound of Formula 1 (free base) disclosed in the prior literature was not very good, in terms of physical properties, to be used as an active pharmaceutical ingredient (API).

First, the compound of Formula 1 was not solidified, which posed great difficulty in controlling a residual solvent. Specifically, it was possible to obtain the compound of Formula 1 in the form of a foam in a case where the compound of Formula 1 in a dissolved state is concentrated and dried in vacuo as much as possible; however, the compound of Formula 1 in the form of a foam was easily moistened and turned into a sticky oil form.

Second, the compound of Formula 1 had poor stability. Specifically, the compound of Formula 1 is decomposed over time to generate related substances because the aminobutyric acid moiety in its structure easily forms a lactam ring.

The present inventors prepared various salts and crystalline forms of the compound of Formula 1, and tested their physical properties. As a result, the present inventors have found that specific salts and crystalline forms of the compound reduces decomposition and hygroscopicity and have good stability, which makes such salts and crystalline forms suitable for pharmaceutical uses such as preparation of pharmaceutical compositions; and thus have completed the present invention.

Accordingly, an object of the present invention is to provide salts and crystalline forms of the furopyrimidine compound of Formula 1, and pharmaceutical uses thereof.

Solution to Problem

The present invention provides a salt of the compound of Formula 1, the salt being selected from the group consisting of besylate salt, hydrochloride salt, oxalate salt, sodium salt, and potassium salt.

[Formula 1]

In addition, the present invention provides a crystalline form of a besylate salt of the compound of Formula 1.

In addition, the present invention provides a pharmaceutical composition comprising the salt or crystalline form, and a pharmaceutically acceptable additive. The pharmaceutical composition is used for prevention or treatment of a sex hormone-related disease.

In addition, the present invention provides a use of the salt or crystalline form for inhibiting a sex hormone-related disease, and a use of the salt or crystalline form for manufacture of a medicament therefor.

In addition, the present invention provides a use of the salt or crystalline form for preventing or treating a sex hormone-related disease, and a use of the salt or crystalline form for manufacture of a medicament therefor.

In addition, the present invention provides a method for preventing or treating a sex hormone-related disease, comprising a step of administering the salt or crystalline form to a subject in need thereof.

Advantageous Effects of Invention

Salts and crystal forms of the compound of Formula 1 according to the present invention are good in terms of various physicochemical properties, that is, hygroscopicity, related substances, physicochemical stability, and the like, and thus can be used for pharmaceutical uses such as preparation of pharmaceutical compositions comprising the same as an active ingredient.

BEST MODE FOR CARRYING OUT THE INVENTION

Hereinafter, the present invention will be described in detail.

<Salt of Compound of Formula 1>

The present invention provides a salt of the compound of Formula 1, the salt being selected from the group consisting of besylate salt, hydrochloride salt, oxalate salt, sodium salt, and potassium salt.

[Formula 1]

The compound of Formula 1 may be prepared according to the method disclosed in Korean Patent No. 1495260 and U.S. Pat. No. 9,481,684, the disclosures of which are incorporated herein by reference in their entireties.

The besylate salt of the compound of Formula 1 is obtained by reaction with benzenesulfonic acid and is also called a benzenesulfonate salt. The besylate salt includes a monobesylate salt containing one besylate group in a molecule, a dibesylate salt containing two besylate groups in a molecule, and the like. Among these, the dibesylate salt is advantageous for crystallization and is more preferred in terms of physicochemical properties.

The hydrochloride salt of the compound of Formula 1 includes a monohydrochloride salt containing one hydrochloride group in a molecule, a dihydrochloride salt containing two hydrochloride groups in a molecule, and the like. Among these, the dihydrochloride salt is more preferred in terms of physicochemical properties.

The oxalate salt of the compound of Formula 1 includes a monooxalate salt containing one oxalate group in a molecule, a dioxalate salt containing two oxalate groups in a molecule, and the like. Among these, the dioxalate salt is more preferred in terms of physicochemical properties.

The sodium or potassium salt of the compound of Formula 1 may contain one sodium or potassium atom in a molecule.

Meanwhile, the compound of Formula 1 (free base) described in the above-mentioned literature was not solidified, and thus was not very good to be used as an active pharmaceutical ingredient (API). However, the salt of the compound of Formula 1 according to the present invention is obtained in a solid state and has good physicochemical properties, which makes such a salt suitable to be used as an active pharmaceutical ingredient.

As a specific example, the salt of the compound of Formula 1 may be a dibesylate salt, a dihydrochloride salt, or a dioxalate salt, which is in a solid state. As a more specific example, the salt of the compound of Formula 1 may be a dibesylate salt in a solid state.

In addition, the salt of the compound of Formula 1 can be applied to preparation of pharmaceutical compositions because such a salt reduces decomposition and hygroscopicity and has good stability.

For example, the salt may have a hygroscopicity of less than 10% by weight, less than 5% by weight, less than 3% by weight, or less than 1% by weight in a case of being left to stand at 25° C. and 60% relative humidity for 1 week. More specifically, the salt may have a hygroscopicity of less than 0.5% by weight in a case of being left to stand at 25° C. and 60% relative humidity for 1 week.

In addition, the salt may have a solubility in water at 25° C. of 10 mg/mL or higher, 15 mg/mL or higher, 20 mg/mL or higher, or 25 mg/mL or higher, and more specifically, 10 mg/mL to 40 mg/mL, 15 mg/mL to 35 mg/mL, or 20 mg/mL to 30 mg/mL.

As an example, the salt may have a hygroscopicity of less than 0.5% by weight in a case of being left to stand at 25° C. and 60% relative humidity for 1 week, and may have a solubility in water at 25° C. of 15 mg/mL or higher.

In addition, the salt may have an increase in related substances of less than 3% by weight, or less than 2% by weight, relative to its initial weight, in a case of being left to stand at 80° C. for 20 hours. Specifically, the salt may have an increase in related substances of less than 1% by weight, relative to its initial weight, in a case of being left to stand at 80° C. for 20 hours. More specifically, the salt may have an increase in related substances of less than 0.5% by weight or less than 0.1% by weight, relative to its initial weight, in a case of being left to stand at 80° C. for 20 hours.

<Crystalline Form of Compound of Formula 1>

The salt of the compound of Formula 1 may be prepared in crystalline form, amorphous form, or as a mixture thereof, with the crystalline form being preferred.

Accordingly, the present invention provides a crystalline form of the besylate salt of the compound of Formula 1.

In general, salts must have various physicochemical properties, such as reproducibility in preparing specific crystalline forms, high crystallinity, stability of crystalline forms, chemical stability, and non-hygroscopicity, to be applied to the pharmaceutical field.

From this point of view, the crystalline form of the besylate salt of the compound of Formula 1 is preferred due to having good stability and physicochemical properties that facilitate formulation. Specifically, the crystalline form may be a crystalline form of a dibesylate salt containing two besylate groups in a molecule.

For the besylate salt of the compound of Formula 1, tests have shown that a specific crystalline form (hereinafter referred to as 'crystalline form A') is more advantageous in terms of non-hygroscopicity and physicochemical stability. Such properties can have a positive effect on dissolution, stability, and physical properties of an active pharmaceutical ingredient as well as its drug product, so that the crystalline form may be more suitable as an active ingredient of a pharmaceutical composition.

On the other hand, the besylate salt of the compound of Formula 1 may exist in at least one crystalline form; however, another crystalline form thus obtained (hereinafter referred to as 'crystalline form B') may be in a relatively metastable crystalline state and undergo some crystalline transitions due to changes over time.

The crystalline form (crystalline form A) of the besylate salt may have a powder X-ray diffraction (PXRD) spectrum including peaks at diffraction angles)(2θ±0.2° of 5.97°, 7.22°, 10.23°, 11.91°, 15.25°, 16.20°, 18.26°, 18.48°, 20.53°, and 23.94°.

In addition, the powder X-ray diffraction (PXRD) spectrum of the crystalline form (crystalline form A) may further include, in addition to the aforementioned peaks, peaks at diffraction angles)(2θ±0.2° of 6.70°, 12.68°, 13.41°, 19.62°, 19.79°, 22.14°, 22.96°, and 24.34°.

In addition, the powder X-ray diffraction (PXRD) spectrum of the crystalline form (crystalline form A) may further include, in addition to the aforementioned peaks, peaks at diffraction angles)(2θ±0.2° of 9.88°, 15.66°, 17.23°, 17.48°, 18.85°, 19.27°, and 29.28°.

The peaks as exemplified above may be peaks having a relative intensity of about 10% or higher, 20% or higher, 30% or higher, or 50% or higher. In the present specification, the relative intensity of a peak is expressed as a percentage of relative intensity ratio ($I/I_0$) where "$I_0$" refers to the maximum peak intensity, which is set to 100, on the PXRD spectrum and "I" refers to the corresponding peak intensity thereon.

The crystalline form (crystalline form A) may have an endothermic peak in a range of 200° C. to 300° C. when measured by differential scanning calorimetry (DSC) analysis under a temperature rise condition of 10° C./min. Here, a maximum of the endothermic peak may exist in a range of about 225° C. to 245° C., or about 232° C. to 236° C. For example, the crystalline form (crystalline form A) may have an endothermic peak which starts at 225° C. to 235° C. and reaches a maximum at about 230° C. to 240° C., when measured by the DSC analysis.

In addition, the crystalline form (crystalline form A) can be applied to preparation of pharmaceutical compositions because such a crystalline form reduces decomposition and hygroscopicity and has good stability.

For example, the crystalline form (crystalline form A) may have a hygroscopicity of less than 10% by weight, less than 5% by weight, less than 3% by weight, less than 1% by weight, or less than 0.5% by weight, in a case of being left to stand at 25° C. and 60% relative humidity for 1 week.

In addition, the crystalline form (crystalline form A) may have a solubility in water at 25° C. of 10 mg/mL or higher, 15 mg/mL or higher, 20 mg/mL or higher, or 25 mg/mL or higher, and more specifically, 10 mg/mL to 40 mg/mL, 15 mg/mL to 35 mg/mL, or 20 mg/mL to 30 mg/mL.

In addition, the crystalline form (crystalline form A) may have an increase in related substances of less than 3% by weight, less than 2% by weight, less than 1% by weight, less than 0.5% by weight, or less than 0.1% by weight, relative to its initial weight, in a case of being left to stand at 80° C. for 20 hours.

The crystalline form (crystalline form A) may be prepared from the compound of Formula 1 or its salt thereof by crystallization using at least one solvent. The solvent used for crystallization may be selected from the group consisting of ethyl acetate, acetone, acetonitrile, and a mixed solvent thereof. Alternatively, the method for preparing a salt of the compound of Formula 1 may be the same as the method for preparing a crystalline form thereof <Pharmaceutical Uses>

As disclosed in U.S. Pat. No. 9,481,684 and the like, it has been proven that the compound of Formula 1 acts as a gonadotropin-releasing hormone (GnRH) receptor antagonist and thus are useful in preventing or treating various sex hormone-related symptoms.

From this point of view, a salt or crystalline form of the compound of Formula 1 can be used for prevention or treatment of a sex hormone-related disease.

As used herein, the term "prevention" refers to any act of inhibiting or delaying occurrence, spread, or recurrence of the disease by administration of the salt or crystalline form of the compound of Formula 1, and the term "treatment" refers to any act of ameliorating or beneficially altering the disease by administration of the salt or crystalline form of the compound of Formula 1.

The present invention provides a use of a salt or crystalline form of the compound of Formula 1, for preventing or treating a sex hormone-related disease. In addition, the present invention provides a use of a salt or crystalline form of the compound of Formula 1, for manufacture of a medicament for preventing or treating a sex hormone-related disease.

In addition, the present invention provides a method for preventing or treating a sex hormone-related disease, comprising a step of administering a salt or crystalline form of the compound of Formula 1 to a subject in need thereof.

As used herein, the term "subject in need thereof" refers to any animal, specifically a mammal, who has or may develop the disease, including humans (patients), monkeys, cattle, horses, sheep, pigs, chickens, turkeys, quails, cats, dogs, mice, rats, rabbits, and guinea pigs. In addition, the subject in need thereof may refer to a biological sample.

In addition, as used herein, the term "administration" refers to providing a predetermined substance to a subject in need thereof by any suitable method. For administration routes of the compound of the present invention, any general route may be used for administration as long as the route allows the compound to reach its target tissue.

In addition, the present invention provides a pharmaceutical composition, comprising the salt or crystalline form, and a pharmaceutically acceptable additive.

The pharmaceutical composition comprising the salt or crystalline form of the compound of Formula 1 may be used for prevention or treatment of a sex hormone-related disease.

For example, the sex hormone-related disease may be selected from the group consisting of prostate cancer, breast cancer, ovarian cancer, uterine cancer, pituitary gland cancer, endometriosis, amenorrhea, menstrual irregularity, uterine myoma, uterine fibroids, polycystic ovarian disease, lupus erythematosus, hirsutism, precocious puberty, short stature, acne, alopecia, gonadotrophic pituitary adenoma, sleep apnea, irritable bowel syndrome, premenstrual syndrome, benign prostatic hyperplasia, infertility, and Alzheimer's disease.

In particular, the pharmaceutical composition comprising the salt or crystalline form of the compound of Formula 1 is effective in preventing or treating endometriosis and uterine myoma.

A dosage of the salt or crystalline form of the compound of Formula 1, or a pharmaceutical composition comprising the same may vary depending on the subject to be treated, the severity of disease or condition, the rate of administration, and the judgment of the prescribing doctor. Usually, based on a case where a free base of the compound of Formula 1 is used as an active ingredient, the compound may be administered to a mammal including humans via an oral or parenteral route in an amount of 0.01 mg/kg (body weight) to 100 mg/kg (body weight), preferably 0.2 mg/kg (body weight) to 50 mg/kg (body weight), once to twice a day or using an on/off schedule. In some cases, a dosage smaller than the above-mentioned range may be more suitable, and a larger dosage may also be used without causing harmful side effects. In a case where a larger dosage is used, the dosage may be divided into several smaller dosages over the day.

The pharmaceutical composition according to the present invention may be formulated according to conventional methods, and may be prepared into various oral dosage forms such as tablets, pills, powders, capsules, syrups, emulsions, and microemulsions, or parenteral dosage forms such as for intramuscular, intravenous, or subcutaneous administration.

The pharmaceutical composition may contain any conventional non-toxic pharmaceutically-acceptable additives, such as carriers, diluents, adjuvants, and excipients. In a case where the pharmaceutical composition according to the present invention is prepared in the form of an oral dosage form, examples of the carrier used include cellulose, calcium silicate, corn starch, lactose, sucrose, dextrose, calcium phosphate, stearic acid, magnesium stearate, calcium stearate, gelatin, talc, surfactants, suspending agents, and emulsifying agents. In addition, in a case where the pharmaceutical composition according to the present invention is prepared in the form of an oral dosage form, examples of the diluent used include lactose, mannitol, sugar, microcrystalline cellulose and cellulose derivatives, and dried corn starch. In a case where the pharmaceutical composition according to the present invention is prepared in the form of an injection, examples of the carrier used include water, saline, an aqueous glucose solution, an aqueous pseudo-sugar solution, alcohol, glycol, ether (for example, polyethylene glycol 400), oil, fatty acid, fatty acid ester, glycerides, surfactants, suspending agents, and emulsifying agents.

MODE FOR THE INVENTION

Hereinafter, the present invention will be described by way of specific examples. However, the following examples are only examples for illustrating the present invention, and the scope of the present invention is not limited thereto.

Preparation Example 1: Preparation of Compound of Formula 1

According to the method in U.S. Pat. No. 9,481,684 as cited herein or a method similar thereto, a free base of the compound of Formula 1, that is, (R)-4-((2-(1-(2-fluoro-6-(trifluoromethyl)benzyl)-2,4-dioxo-1'-((5-(trifluoromethyl)furan-2-yl)methyl)-1H-spiro[furo[3,4-d]pyrimidine-5,4'-piperidine]-3 (2H,4H,7H)-yl)-1-phenylethyl)amino)butanoic acid, was obtained in the form of a white foam.

$^1$H-NMR (600 MHz, DMSO-$d_6$) δ 1.39 (d, 1H, J=11.5 Hz), 1.43-1.52 (m, 3H), 2.00 (td, 1H, J=13.2, 4.5 Hz), 2.09-2.21 (m, 4H), 2.21-2.31 (m, 3H), 2.63-2.72 (m, 2H), 3.60 (s, 2H), 3.78-3.87 (m, 2H), 3.87-3.94 (m, 1H), 4.88 (s, 2H), 4.98 (s, 2H), 6.53 (d, 1H, J=3.4 Hz), 7.12-7.19 (m, 4H), 7.22 (t, 2H, J=7.3 Hz)), 7.52-7.62 (m, 2H), 7.62-7.66 (m, 1H).

<Preparation of Salt of Compound of Formula 1>

Example 1. Preparation of Dibesylate Salt of Compound of Formula 1

An ethyl acetate/acetone (1/3, v/v) solution (20 mL) of the compound of Formula 1 (free base, 2.0 g) was cooled to 5° C., and then 2.2 equivalents of benzenesulfonic acid (2 M solution in acetone, 2.9 mL) were added thereto. Stirring was performed at 5° C. for 3 hours under nitrogen atmosphere, and then stirring was performed at room temperature for 12 hours. The resulting solid was filtered and dried in vacuo at room temperature for 12 hours, to obtain 2.6 g of a white solid (91% yield).

$^1$H-NMR (600 MHz, DMSO-$d_6$) δ 1.56 (d, 1H, J=14.6 Hz), 1.67-1.80 (m, 3H), 2.13 (t, 1H, J=12.1 Hz), 2.23 (td, 2H, J=7.2, 3.0 Hz), 2.27-2.35 (m, 1H), 2.59-2.68 (m, 1H), 2.86-2.94 (m, 1H), 3.09-3.20 (m, 2H), 3.32-3.51 (m, 2H), 4.08-4.18 (m, 1H), 4.40-4.51 (m, 2H), 4.57 (s, 2H), 4.98 (s, 2H), 4.99 (s, 2H), 6.93 (s, 1H), 7.22 (s, 1H), 7.23 (s, 1H), 7.27-7.40 (m, 10H), 7.57-7.68 (m, 7H), 9.01 (br s, 1H), 9.08 (br s, 1H), 9.97 (br s, 1H), 12.22 (br s, 1H).

$^{13}$C-NMR (600 MHz, DMSO-$d_6$) δ 21.12, 30.33, 31.11, 31.23, 41.80, 43.82, 45.06, 48.13, 50.57, 59.21, 69.05, 82.90, 109.39, 114.46, 115.73, 116.17, 117.94, 119.71, 120.76, 120.90, 121.48, 121.75, 121.84, 122.50, 122.60, 124.42, 125.52, 127.73, 128.19, 128.62, 128.69, 128.80, 129.43, 130.39, 130.47, 132.07, 141.26, 147.84, 147.92, 151.10, 153.85, 157.47, 160.23, 161.87, 173.47.

Example 2. Preparation of Dihydrochloride Salt of Compound of Formula 1

A 1,4-dioxane solution (50 mL) of the compound of Formula 1 (free base, 1.4 g) was cooled to 5° C., and then 2.2 equivalents of hydrochloric acid (350 μL of concentrated HCl aqueous solution) were added thereto. Stirring was performed at room temperature for 1 hour. To the reaction solution was added sodium sulfate. The resultant was dried and filtered, and then washed with 1,4-dioxane (10 mL). The filtrate was concentrated under reduced pressure to a volume of ⅕. The resulting solid was filtered and dried in vacuo at room temperature for 24 hours, to obtain 1.5 g of a white solid (yield: 94%).

$^1$H-NMR (400 MHz, MeOD-$d_4$) 1.85-2.03 (m, 4H), 2.40 (t, 2H, J=6.9 Hz), 2.43-2.60 (m, 2H), 2.80-2.89 (m, 1H), 2.95-3.04 (m, 1H), 3.33-3.42 (m, 2H), 3.45-3.55 (m, 2H), 4.42 (dd, 1H, J=13.7, 7.5 Hz), 4.51 (dd, 1H, J=13.8, 6.7 Hz), 4.56 (s, 2H), 4.66 (t, 1H, J=7.1 Hz), 5.02 (s, 2H) 5.13 (dd, 2H, J=32.2, 16.2 Hz), 6.96 (d, 1H, J=3.3 Hz), 7.15 (d, 1H, J=2.8 Hz), 7.37-7.47 (m, 6H), 7.58-7.66 (m, 2H).

Example 3. Preparation of Dioxalate Salt of Compound of Formula 1

An ethyl acetate solution (10 mL) of the compound of Formula 1 (free base, 1.5 g) was cooled to 5° C., and then 2.2 equivalents of oxalic acid (0.55 M solution in ethyl acetate, 8 mL) were added thereto. Stirring was performed at room temperature for 4 hours under nitrogen atmosphere. The reaction solution was concentrated to a volume of ½ and stirred at 5° C. for 5 hours. The resulting solid was filtered and dried in vacuo at room temperature for 12 hours, to obtain 1.8 g of a white solid (yield: 93%).

$^1$H-NMR (300 MHz, MeOD-$d_4$) δ 1.78-1.98 (m, 4H), 2.33 (t, 2H, J=7.0 Hz), 2.40-2.60 (m, 2H), 2.71-2.82 (m, 1H), 2.87-2.98 (m, 1H), 3.22-3.29 (m, 2H), 3.42-3.51 (m, 2H), 4.32 (dd, 1H, J=13.3, 6.4 Hz), 4.44-4.51 (m, 3H), 4.70 (dd, 1H, J=8.3, 6.0 Hz), 4.96 (s, 2H), 5.13 (dd, 2H, J=42.8, 16.2 Hz), 6.88 (d, 1H, J=3.4 Hz), 7.07-7.11 (m, 1H), 7.37-7.44 (m, 6H), 7.52-7.64 (m, 2H).

Example 4. Preparation of Sodium Salt of Compound of Formula 1

To a solution (5 mL) of the compound of Formula 1 (free base, 1.5 g) in methanol were added 1.1 equivalents of sodium hydroxide (2 mL of methanol solution). Stirring was performed at room temperature for 2 hours. The reaction solution was concentrated. Then, addition of distilled water (13 mL) and n-butanol (12 mL) was performed. Addition of 30 wt % aqueous NaOH solution (2 mL) was performed. The reaction solution was shaken to separate the layers. Then, the organic layer was recovered, and the aqueous layer was extracted twice more with n-butanol (5 mL). The organic layer was collected and washed sequentially with saturated aqueous sodium chloride solution (10 mL) and distilled water (10 mL). The organic layer was concentrated and dried in vacuo to obtain a yellow foam. This was dissolved in methyl t-butyl ether (MTBE, 20 mL), and then filtered through a polytetrafluoroethylene (PTFE) membrane (0.45 μm). The filtrate was concentrated. The concentrate was dissolved in MTBE (2 mL), and then stirred while slowly adding n-heptane (10 mL). The resultant was stirred for an additional hour, filtered, and dried in vacuo, to obtain 1.2 g of a white solid (yield: 82%).

$^1$H-NMR (300 MHz, CDCl$_3$) δ 1.30-1.57 (m, 4H), 1.88-2.02 (m, 2H), 2.11-2.35 (m, 6H), 2.63-2.74 (m, 2H), 3.54 (s, 2H), 3.87-4.09 (m, 3H), 4.57 (s, 2H), 4.96-5.11 (m, 2H), 6.25 (d, 1H, J=3.2 Hz), 6.65-6.69 (m, 1H), 7.05-7.24 (m, 6H), 7.34-7.49 (m, 2H).

Example 5. Preparation of Potassium Salt of Compound of Formula 1

To a methanol solution (5 mL) of the compound of Formula 1 (free base, 1.5 g) were added 1.1 equivalents of potassium hydroxide (2 mL of methanol solution). Stirring was performed at room temperature for 17 hours. The reaction solution was concentrated. Then, addition of distilled water (13 mL) and n-butanol (12 mL) was performed. Addition of 30 wt % aqueous KOH solution (2 mL) was performed. The reaction solution was shaken to separate the layers. Then, the organic layer was recovered, and the aqueous layer was extracted once more with n-butanol (10 mL). The organic layer was collected and washed sequentially with saturated aqueous potassium chloride solution (10 mL) and distilled water (10 mL). The organic layer was concentrated and dried in vacuo to obtain a yellow foam. This was dissolved in methyl t-butyl ether (MTBE, 20 mL), and then filtered through a polytetrafluoroethylene (PTFE) membrane (0.45 μm). The filtrate was concentrated. The concentrate was dissolved in MTBE (2 mL), and then stirred while slowly adding n-heptane (10 mL). The resultant was stirred for an additional hour, filtered, and dried in vacuo, to obtain 1.3 g of a white solid (yield: 84%).

$^1$H-NMR (300 MHz, CDCl$_3$) δ 1.26-1.54 (m, 4H), 1.85-1.97 (m, 2H), 2.08-2.35 (m, 6H), 2.64-2.74 (m, 2H), 3.54 (s, 2H), 3.89-4.06 (m, 3H), 4.58 (s, 2H), 5.02 (s, 2H), 6.25 (d, 1H, J=3.1 Hz), 6.66-6.70 (m, 1H), 7.05-7.24 (m, 6H), 7.36-7.49 (m, 2H).

Comparative Example 1. Preparation of Diphosphate Salt of Compound of Formula 1

A dichloromethane solution (2 mL) of the compound of Formula 1 (free base, 1.5 g) was cooled to 5° C., and then 2.2 equivalents of phosphoric acid (1 M solution in ethanol, 4.4 mL) were added thereto. Stirring was performed at room temperature for 12 hours under nitrogen atmosphere. The reaction solution was concentrated under reduced pressure, dissolved in 5 mL of ethanol, and stirred at 5° C. for 5 hours under nitrogen atmosphere. The reaction solution was concentrated under reduced pressure, and then dried in vacuo at room temperature for 12 hours, to obtain 1.9 g of a white foam (yield: 98%).

$^1$H-NMR (300 MHz, MeOD-$d_4$) δ 1.73-1.92 (m, 4H), 2.33 (t, 2H, J=6.9 Hz), 2.37-2.56 (m, 2H), 2.69-2.89 (m, 2H), 3.06 (t, 2H, J=11.2 Hz), 3.22-3.32 (m, 2H), 4.28 (s, 2H), 4.33-4.43 (m, 2H), 4.56 (t, 1H, J=7.1 Hz), 4.91 (s, 2H), 4.99-5.12 (m, 2H), 6.85 (d, 1H, J=3.5 Hz), 7.01-7.05 (m, 1H), 7.30-7.41 (m, 6H), 7.48-7.60 (m, 2H).

Comparative Example 2. Preparation of Disulfate Salt of Compound of Formula 1

A dichloromethane solution (1 mL) of the compound of Formula 1 (free base, 0.50 g) was cooled to 5° C., and then 2.2 equivalents of sulfuric acid (solution obtained by dissolving 77 μL of sulfuric acid in 1 mL of dichloromethane) were added thereto. Stirring was performed at room temperature for 1 hour under nitrogen atmosphere. The reaction solution was concentrated under reduced pressure and dried in vacuo at room temperature for 12 hours, to obtain 0.40 g of a white foam (yield: 64%).

$^1$H-NMR (300 MHz, MeOD-$d_4$) δ 1.65-1.90 (m, 4H), 2.34-2.54 (m, 4H), 2.76-2.92 (m, 4H), 3.16 (d, 2H, J=12.0 Hz), 4.13 (s, 2H), 4.32-4.47 (m, 2H), 4.59 (t, 1H, J=7.2 Hz), 4.93 (s, 2H), 5.02-5.15 (m, 2H), 6.80 (d, 1H, J=3.5 Hz), 7.00-7.04 (m, 1H), 7.35-7.44 (m, 6H), 7.52-7.63 (m, 2H).

Comparative Example 3. Preparation of Ditosylate Salt of Compound of Formula 1

A dichloromethane solution (1 mL) of the compound of Formula 1 (free base, 0.50 g) was cooled to 5° C., and then 2.2 equivalents of tosylic acid (solution obtained by dissolving 276 mg of tosylic acid in 1 mL of ethanol/ethyl acetate (3/7, v/v)) were added thereto. Stirring was performed at room temperature for 12 hours under nitrogen atmosphere. The reaction solution was concentrated under reduced pressure, and then dried in vacuo at room temperature for 12 hours, to obtain 0.59 g of a white foam (yield: 81%).

$^1$H-NMR (300 MHz, MeOD-$d_4$) δ 1.76-1.86 (m, 2H), 1.90-1.98 (m, 2H), 2.22 (t, 2H, J=7.0 Hz), 2.37 (s, 6H), 2.40-2.58 (m, 2H), 2.68-2.78 (m, 1H), 2.82-2.92 (m, 1H), 3.33-3.41 (m, 2H), 3.44-3.54 (m, 2H), 4.33-4.48 (m, 2H), 4.54 (s, 2H), 4.61-4.66 (m, 1H), 4.98 (s, 2H), 5.12 (dd, 2H, J=36.9, 16.2 Hz), 6.93 (d, 1H, J=6.94 Hz), 7.11-7.14 (m, 1H), 7.24 (d, 4H), 7.36-7.45 (m, 6H), 7.54-7.64 (m, 2H), 7.69-7.73 (m, 4H).

<Evaluation of Physical Properties of Salt of Compound of Formula 1>

Test Example 1. Hygroscopicity

Each of the salts (dibesylate salt, dihydrochloride salt, dioxalate salt, sodium salt, potassium salt) prepared in the above examples was left to stand at 25° C. and 60% or 90% relative humidity for 1 week, and a hygroscopicity thereof was measured. Here, the hygroscopicity was measured as a percentage of weight increase, which was measured after the hygroscopicity test, relative to the initial weight. The results are shown in Table 1 below.

TABLE 1

| Hygroscopicity | Dibesylate salt | Dihydrochloride salt | Dioxalate salt | Sodium salt | Potassium salt |
| --- | --- | --- | --- | --- | --- |
| 25° C., 60% RH | 0.06 wt % | 2.1 wt % | 3.5 wt % | 8.7 wt % | 9.2 wt % |
| 25° C., 90% RH | 0.9 wt % | 16 wt % | 19 wt % | 35 wt % | 38 wt % |

As shown in the above table, the salts in the examples exhibited a low hygroscopicity under 25° C. and 60% relative humidity, and in particular, the dibesylate salt in Example 1 exhibited a very low hygroscopicity even under 25° C. and 90% relative humidity. On the contrary, the salts prepared in the comparative examples, that is, the diphosphate salt, the disulfate salt, and the ditosylate salt were obtained in the form of a foam like the free base, and were easily moistened and turned into a sticky oil form.

Test Example 2. Chemical Purity

Each of the salts (dibesylate salt, dihydrochloride salt, sodium salt, potassium salt) prepared in the above examples was left to stand at 80° C. for 20 hours, and then an amount of change in related substances was measured. In addition, each of the salts was left to stand at 80° C. for 21 days, and then a residual amount of the main compound (compound of Formula 1) was measured. For measurement of the related substances and the main compound, samples were taken before and after exposure to 80° C., dissolved in a diluted solution at a concentration of 1 mg/mL, and then subjected to high-performance liquid chromatography (HPLC). From the resulting data, an increase in related substances was calculated by measuring a peak area of lactam-based related substances relative to a peak area of the main compound. In addition, for comparison, the same test was also carried out for the free base of the compound of Formula 1. The results are shown in Tables 2 and 3 below.

In addition, in a similar manner, the dibesylate salt prepared in the above example was stored for 3 months (at 40° C. and 75% relative humidity), and amounts of change in lactam-based related substances and main compound were measured. The results were shown in Table 4 below.

TABLE 2

| Increase in related substances | Free base | Dibesylate salt | Dihydrochloride salt | Sodium salt | Potassium salt |
| --- | --- | --- | --- | --- | --- |
| After 20 hours at 80° C. | 79.0% | 0.0% | 0.9% | 0.6% | 0.4% |

TABLE 3

| Residual amount of main compound | Free base | Dibesylate salt | Dihydrochloride salt | Sodium salt | Potassium salt |
| --- | --- | --- | --- | --- | --- |
| After 21 days at 80° C. | 1.4% | 99.6% | 69.4% | 77.0% | 72.6% |

TABLE 4

| Chemical purity | Initial | After 3 months |
| --- | --- | --- |
| Related substances | 0.02% | 0.03% |
| Dibesylate salt | 99.7% | 99.6% |

As shown in Tables 2 and 3, the free base exhibited an increase in related substances by about 79%, whereas the salts in the examples exhibited a small increase in related substances and thus had good stability. In particular, the dibesylate salt in Example 1 did not generate any related substances and thus had very good stability. In addition, as shown in Table 4, it was identified that the salts in the examples were very stable even in a case of being left to stand at 40° C. and 75% relative humidity for 3 months.

Test Example 3. Water Solubility

The dibesylate salt, which showed the best results in the hygroscopicity and stability tests, was compared with the free base in terms of water solubility. The water solubility was obtained as follows. Each of the free base and the dibesylate salt was dissolved in distilled water at 25° C. to make it supersaturated. Then, the solution was taken and diluted 20-fold with a diluent for dissolution. Then, the resultant was subjected to high-performance liquid chromatography (HPLC). In the resulting data, the dissolved amount was calculated from a peak area of the main compound. The results are shown in Table 5 below.

TABLE 5

|  | Free base | Dibesylate salt |
|---|---|---|
| Water solubility (25° C.) | 0.19 mg/mL | 25.77 mg/mL |

As shown in Table 5, the dibesylate salt exhibited a greatly improved water solubility as compared with a low water solubility of the free base. This increase in water solubility improves disintegration and dissolution rate in its drug product, which makes the compound highly desirable for use as an active pharmaceutical ingredient (API).

Test Example 4. Stability of Drug Product

Using each of the salts (dibesylate salt, dihydrochloride salt, sodium salt, potassium salt) prepared in the above examples, a drug product was prepared in the form of an oral capsule with the excipient composition as shown in Table 6 below. The drug product was left to stand at 50° C. and 80% humidity for 3 weeks, and then an amount of change in related substances was measured. For measurement of related substances, the contents were separated from the capsule, and then all of them were placed in a diluted solution so that the active ingredient was brought to a concentration of 1 mg/mL. Shaking was performed for 5 minutes. The supernatant was taken and filtered. The filtrate was taken and subjected to high-performance liquid chromatography (HPLC).

From the resulting data, percentages of a peak area of the main compound (active ingredient) and a peak area of the lactam-based related substances were measured. In addition, for comparison, the same test was also carried out for the free base of the compound of Formula 1. The salts and the free base used in the test all had a chemical purity of 98% or higher. The results are shown in Table 7 below.

TABLE 6

| Ingredient | Role | Amount |
|---|---|---|
| Free base or salt | Active ingredient | 3 mg |
| Silicon oxide | Lubricant | 0.6 mg |
| Lactose hydrate | Filler | 121 mg |
| Crospovidone | Disintegrant | 15 mg |
| Talc | Glidant | 1.2 mg |

TABLE 7

| Stability of drug product | Active ingredient | Related substances |
|---|---|---|
| Free base-based drug product | 14.6% | 80.6% |
| Dibesylate salt-based drug product | 98.3% | 0.60% |
| Sodium salt-based drug product | 55.7% | 37.3% |
| Potassium salt-based drug product | 60.9% | 31.0% |
| Hydrochloride salt-based drug product | 49.7% | 41.4% |

As shown in Table 7, the salts in the examples maintained a high chemical purity as compared with the free base. In particular, the dibesylate salt in Example 1 exhibited very good stability. On the contrary, the free base-based drug product exhibited greatly decreased stability in a case of being stored at 50° C. and 80% relative humidity for 3 weeks.

<Crystal Analysis of Dibesylate Salt of Compound of Formula 1>

Test Example 5. Powder X-Ray Diffraction (PXRD)

Figure 1:
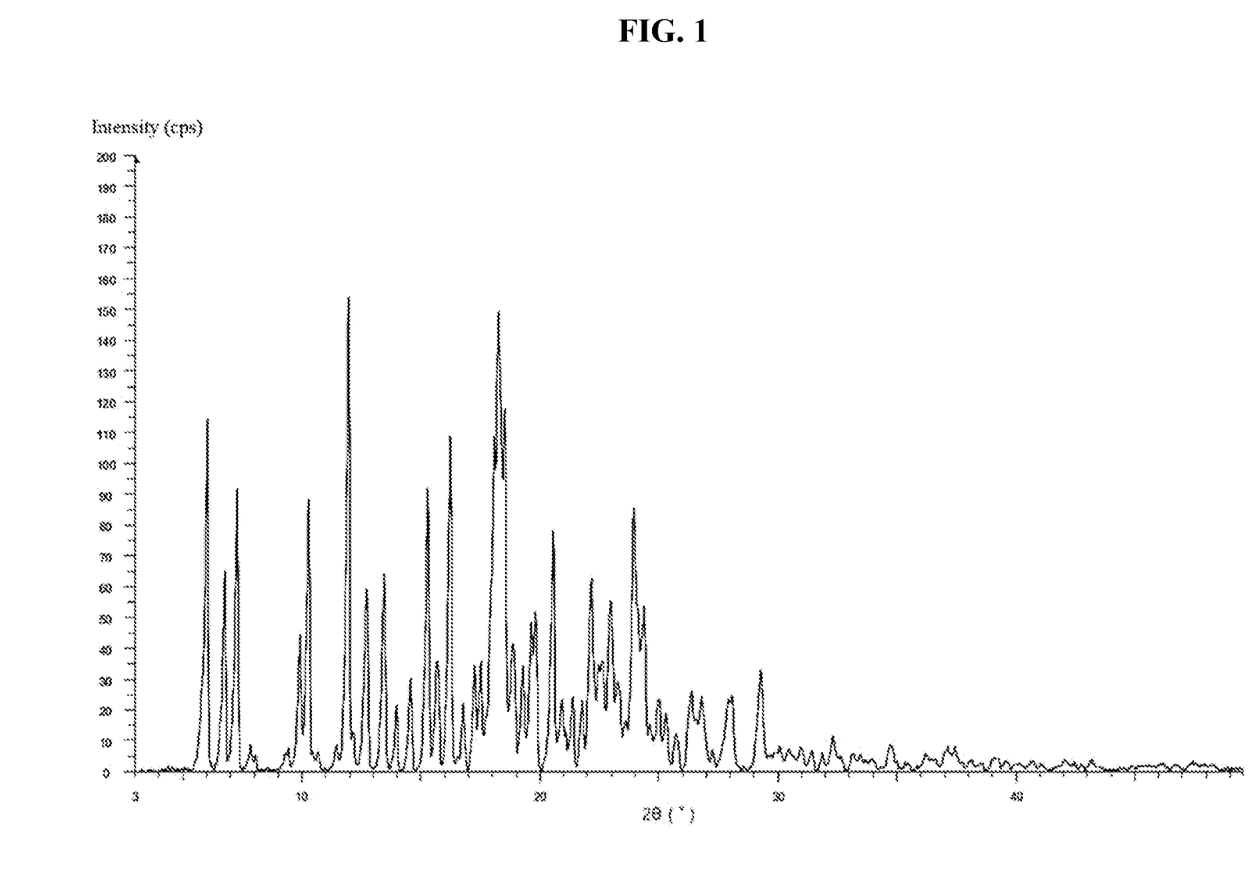
FIGS. 1 to 3 illustrate powder X-ray diffraction (PXRD) spectrum, infrared (IR) spectrum, and differential scanning calorimetry (DSC) curve, respectively, of a crystalline form of the dibesylate salt of the compound of Formula 1 according to Example 1.

The solid product (crystalline form A) obtained in Example 1 was subjected to powder X-ray diffraction (PXRD). The results are shown in FIG. 1 and Table 8 below.

Instrument: Maker Bruker AXS, D8 FOCUS

Conditions: 40 kV, 30 mA, 2θ/θ scan range of 3° to 50°

TABLE 8

| 2θ (°) | d value (Å) | Intensity (cps) | Relative intensity (%) |
|---|---|---|---|
| 5.97 | 14.80 | 114 | 74.1 |
| 6.70 | 13.18 | 65 | 42.2 |
| 7.22 | 12.23 | 91.6 | 59.4 |
| 9.88 | 8.95 | 44.2 | 28.7 |
| 10.23 | 8.64 | 88.1 | 57.2 |
| 11.91 | 7.43 | 154 | 100 |
| 12.68 | 6.98 | 59.2 | 38.4 |
| 13.41 | 6.60 | 63.9 | 41.5 |
| 13.95 | 6.35 | 21 | 13.6 |
| 14.53 | 6.09 | 29.8 | 19.3 |
| 15.25 | 5.81 | 91.8 | 59.6 |
| 15.66 | 5.65 | 35.6 | 23.1 |
| 16.20 | 5.47 | 109 | 70.6 |
| 16.76 | 5.29 | 21.4 | 13.9 |
| 17.23 | 5.14 | 33.9 | 22 |
| 17.48 | 5.07 | 35.4 | 23 |
| 18.26 | 4.86 | 150 | 97 |
| 18.48 | 4.80 | 118 | 76.3 |
| 18.85 | 4.70 | 41.3 | 26.8 |
| 19.27 | 4.60 | 34.1 | 22.1 |
| 19.62 | 4.52 | 48.1 | 31.2 |
| 19.79 | 4.48 | 51.3 | 33.3 |
| 20.53 | 4.32 | 78.1 | 50.7 |
| 22.14 | 4.01 | 62.3 | 40.5 |
| 22.96 | 3.87 | 55.1 | 35.8 |
| 23.94 | 3.71 | 85.5 | 55.5 |
| 24.34 | 3.65 | 53.8 | 34.9 |
| 26.35 | 3.38 | 25.6 | 16.6 |
| 26.80 | 3.32 | 24.1 | 15.6 |
| 28.04 | 3.18 | 24.1 | 15.6 |
| 29.28 | 3.05 | 32.6 | 21.2 |

Test Example 6. Infrared (IR) Spectroscopy

Figure 2:
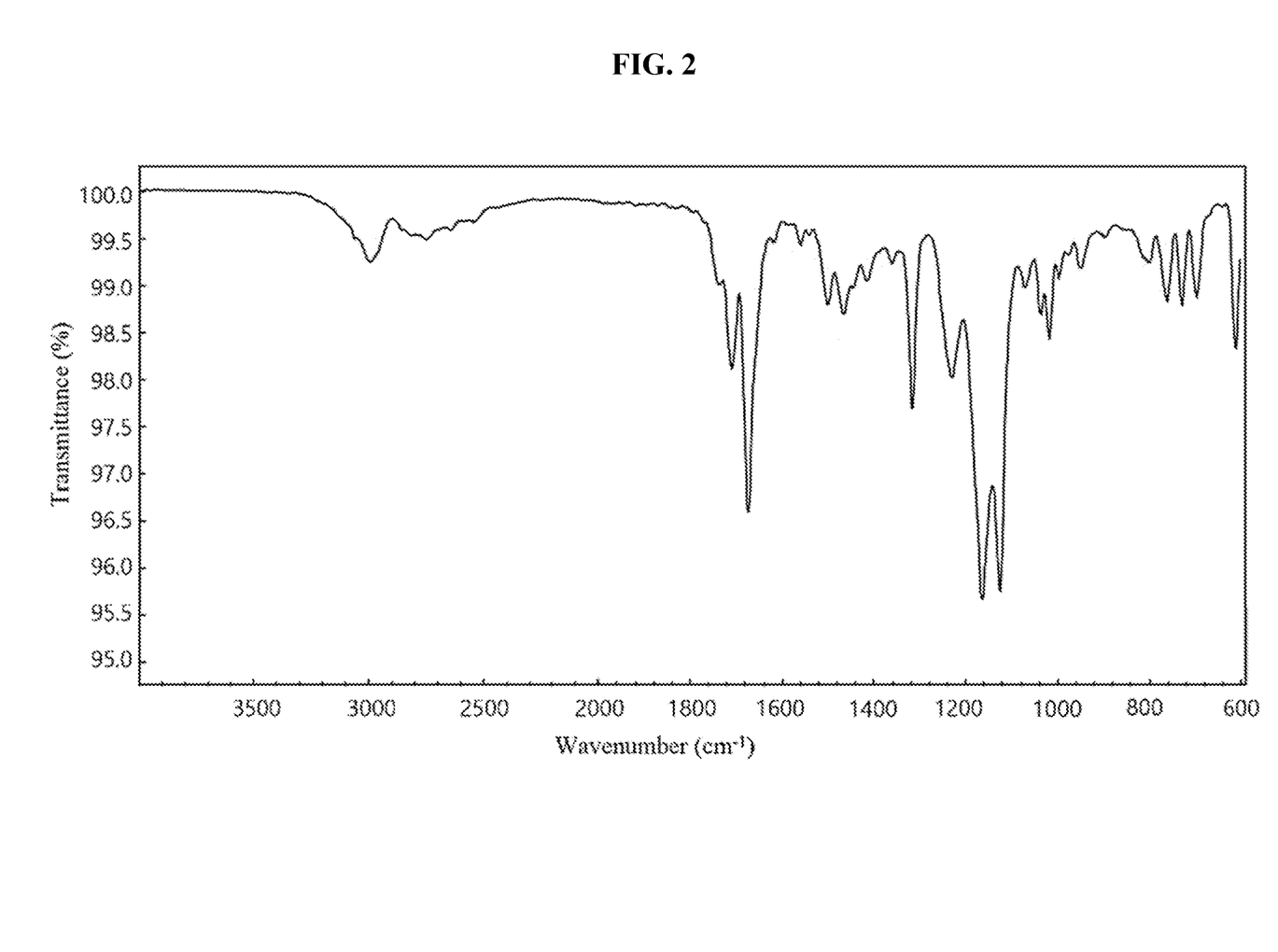

The solid product (crystalline form A) obtained in Example 1 was subjected to infrared (IR) spectroscopy. The instrument and conditions for the infrared spectroscopy, and the results thereof are shown in Table 9 and FIG. 2 below.

TABLE 9

| Instrument | Agilent (Cary670) | |
|---|---|---|
| Analysis conditions | Zn/Se CrystalATR, resolution: 4 cm$^{-1}$, number of scans: 16 | |
| Results | 1125, 1163 cm$^{-1}$ | —CF$_3$ |
|  | 1316 cm$^{-1}$ | —CO$_2$H(—C—O—) |
|  | 1672 cm$^{-1}$ | —CONH—(C=O) |

TABLE 9-continued

| 1707 cm$^{-1}$ | —CO$_2$H(C=O) |
| 2450 to 3200 cm$^{-1}$ | —NH— |

Test Example 7. Differential Scanning Calorimetry (DSC)

Figure 3:
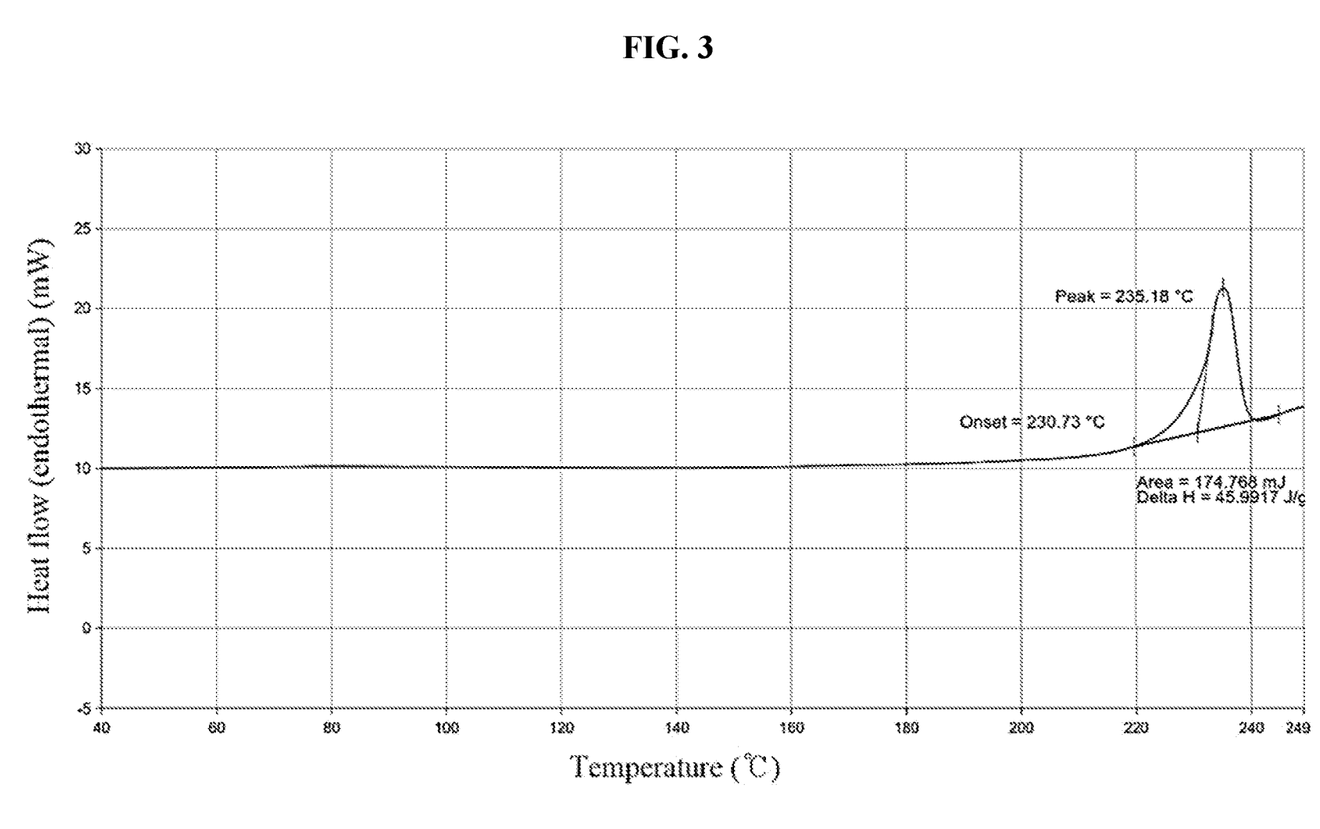

Differential scanning calorimetry (DSC) was performed on the solid product (crystalline form A) obtained in Example 1. The results are illustrated in FIG. 3.
Instrument: PERKIN ELMER DSC8000
Analysis conditions: Sample of 3.8 mg, temperature rise of 10° C. per minute
As illustrated in FIG. 3, the DSC curve shows an endothermic peak that starts at 230.73° C. and reaches a maximum at about 235.18° C.

Test Example 8. Evaluation of Stability of Crystal Form

Figure 4:
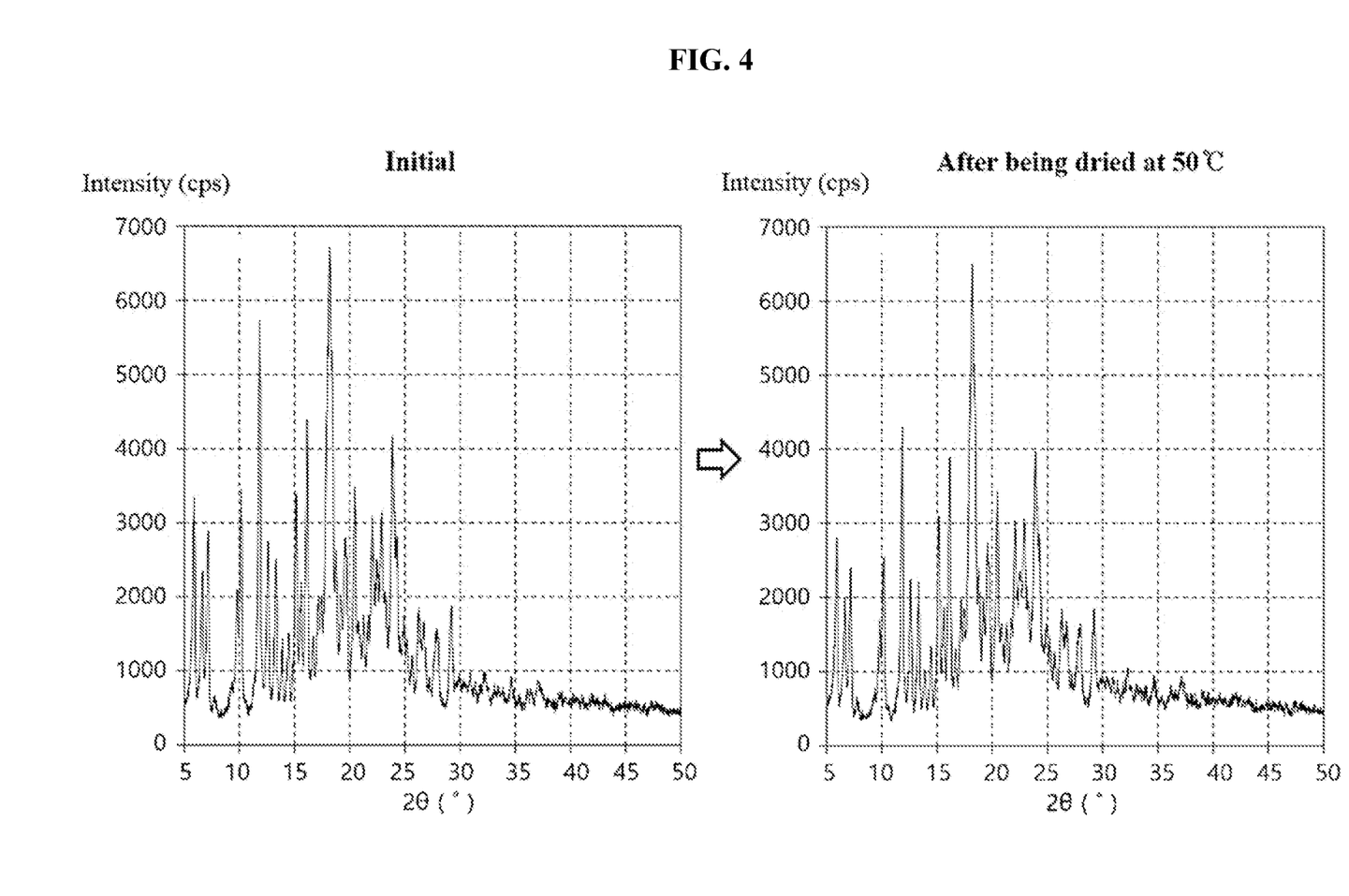
FIG. 4 illustrates powder X-ray diffraction (PXRD) spectra of a crystalline form of the dibesylate salt of the compound of Formula 1 according to Example 1, respectively, before and after storage at 50° C.

The solid product (crystalline form A) obtained in Example 1 was dried in vacuo at 50° C., and then subjected to powder X-ray diffraction as described above. The results are illustrated in FIG. 4.
As illustrated in FIG. 4, it was found that the solid product (crystalline form A) obtained in Example 1 maintained the same crystal structure as its initial one even after being dried in vacuo at 50° C., and thus had good stability.
On the other hand, using 1,4-dioxane as a solvent, a solid product (crystalline form B) was obtained in a similar manner as in Example 1, and subjected to powder X-ray diffraction as described above. As a result, it was identified that this solid product did not maintain some of its initial crystal structure after being dried in vacuo at 50° C., and thus had relatively low stability as compared with the solid product (crystalline form A) obtained in Example 1.

The invention claimed is:

1. A dibesylate salt of the compound of Formula 1:

[Formula 1]

2. The dibesylate salt of claim 1, which is in a solid state.

3. The dibesylate salt of claim 1, which has a hygroscopicity of less than 0.5% by weight in a case of being left to stand at 25° C. and 60% relative humidity for 1 week, and has a solubility in water at 25° C. of 15 mg/mL or higher.

4. A crystalline form of a dibesylate salt of the compound of Formula 1:

[Formula 1]

5. The crystalline form of claim 4, wherein the crystalline form has a powder X-ray diffraction (PXRD) spectrum including at least four peaks at diffraction angles) (2θ+0.2° of 5.97°, 7.22°, 11.91°, 15.25°, 16.20°, 18.26°, and 18.48°.

6. The crystalline form of claim 4, wherein the crystalline form has a maximum of an endothermic peak in a range of 225° C. to 245° C. when measured by differential scanning calorimetry (DSC) analysis under a temperature rise condition of 10° C./min.

7. A pharmaceutical composition comprising:
the dibesylate salt of claim 1; and
a pharmaceutically acceptable additive.

8. A method for treating a sex hormone-related disease in a subject in need thereof comprising administering an effective amount of the pharmaceutical composition of claim 7 to the subject.

9. The method of claim 8, wherein the sex hormone-related disease is selected from the group consisting of prostate cancer, breast cancer, ovarian cancer, uterine cancer, pituitary gland cancer, endometriosis, amenorrhea, menstrual irregularity, uterine myoma, uterine fibroids, polycystic ovarian disease, lupus erythematosus, hirsutism, precocious puberty, short stature, acne, alopecia, gonadotrophic pituitary adenoma, sleep apnea, irritable bowel syndrome, premenstrual syndrome, benign prostatic hyperplasia, infertility, and Alzheimer's disease.

10. A method for treating a sex hormone-related disease in a subject in need thereof, comprising administering an effective amount of the crystallized form of claim 4 to the subject.

11. The crystalline form of claim 5, wherein the crystalline form has a PXRD spectrum comprising further at least one peaks at diffraction angles (2θ+0.2°) of 10.23°, 20.53°, and 23.94°.

12. The crystalline form of claim 4, wherein the crystalline form has a PXRD pattern with characteristic peaks substantially shown in FIG. 1.

13. The crystalline form of claim 4, wherein the crystalline form has a differential scanning calorimetry (DSC) thermograph having an exotherm peak at a temperature of about 235.18° C. when measured by DSC analysis under a temperature rise condition of 10° C./min.

14. The crystalline form of claim 13, wherein the crystalline form has a DSC pattern with characteristic peaks substantially shown in FIG. 3 when measured by DSC analysis under a temperature rise condition of 10° C./min.

15. The method of claim 10, wherein the sex hormone-related disease is selected from the group consisting of prostate cancer, breast cancer, ovarian cancer, uterine cancer, pituitary gland cancer, endometriosis, amenorrhea, menstrual irregularity, uterine myoma, uterine fibroids, polycystic ovarian disease, lupus erythematosus, hirsutism, precocious puberty, short stature, acne, alopecia, gonadotrophic pituitary adenoma, sleep apnea, irritable bowel syndrome, premenstrual syndrome, benign prostatic hyperplasia, infertility, and Alzheimer's disease.

* * * * *